(12) United States Patent
Aida

(10) Patent No.: US 6,316,184 B1
(45) Date of Patent: Nov. 13, 2001

(54) METHOD FOR JUDGING THE POSSIBILITY OF THE ONSET OF SHEEP LEUKEMIA

(75) Inventor: Yoko Aida, Tsukuba (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/355,947

(22) PCT Filed: Feb. 16, 1998

(86) PCT No.: PCT/JP98/00620

§ 371 Date: Oct. 21, 1999

§ 102(e) Date: Oct. 21, 1999

(87) PCT Pub. No.: WO98/36092

PCT Pub. Date: Aug. 20, 1998

(30) Foreign Application Priority Data

Feb. 17, 1997 (JP) .................................................... 9-031787

(51) Int. Cl.[7] .............................. C12Q 1/68; C12Q 1/70; C07H 21/04

(52) U.S. Cl. ..................................... 435/5; 435/6; 435/84; 435/85; 435/89; 435/91.1; 435/91.2; 536/24.31; 536/24.33; 935/77; 935/78

(58) Field of Search .............................. 435/5, 6, 84, 85, 435/89, 91.1, 91.2; 536/24.33, 24.31; 935/77, 78

(56) References Cited

U.S. PATENT DOCUMENTS 5,582,987 * 12/1996 Lewin et al. ............................. 435/6

OTHER PUBLICATIONS

Brooker; Genetics:Analysis and Principles, p. 79, 1998.*

19th Congress of the Molecular Biology Society of Japan, Sapporo–shhi, Aug. 28, 1996, Presentation No. 3–P–1124, Abstracts p. 526, published on Jul. 25, 1996, with an English language translation.

Aida et al., Jikken Igaku ≡Experimental Medicine , Extra volume, "AIDS and ATL, from Molecular Level Consideration to Prevention and Treatment", 11(5), pp. 547–557, 1993.

Aida et al., Biochem. Biophys. Res. Commun., 209, 981–988, 1995.

Aida et al., Am. J. Vet. Res., 50, pp. 1946–1951, 1989.

Schwaiger et al., Mol. Biol. Evol., 11, pp. 239–249, 1994.

Ballingall et al., Animal Genetics, 23, pp. 347–359, 1992.

Hughes, Cell, 15, pp. 1397–1410, 1978.

McKnight, Cell, 14, pp. 403–413, 1978.

Miyasaka et al., Z., Immunological Methods, vol. 3, pp. 403–423, 1985.

* cited by examiner

Primary Examiner—Lynette R. F. Smith
Assistant Examiner—Padma Baskar
(74) Attorney, Agent, or Firm—Greenblum & Bernstein, P.L.C.

(57) ABSTRACT

There is provided a method for convenient judgement of a possibility of the onset of leukemia of an ovine individual caused by the bovine leukemia virus (BLV) by means of genetic engineering techniques.

A method for judging a possibility of the onset of ovine leukemia caused by bovine leukemia virus (BLV), wherein an ovine individual, in which an amino acid sequence defined by the amino acid numbers of 70 and 71 of the β1 domain of the ovine MHC Class II DRβ chain is Ser-Arg or Gln-Thr, is judged to have a risk of the onset of the leukemia, or an ovine individual, in which the amino acid sequence is Arg-Lys, is judged to have resistance to the onset of the leukemia.

6 Claims, 3 Drawing Sheets

Fig. 1

<u>ggaattcctctctct</u>GCAGCACATTTCCTGGAGTATTCT
                              GluTyrSer ACGGAGCGAGTGTCATTTCTTCAACGGGACGGAGCGGTG
ThrSerGluCysHisPhePheAsnGlyThrGluArgVal CGGTTCCTGGACAGATACTTCTATAATGGAGAAGAGTAC
ArgPheLeuAspArgTyrPheTyrAsnGlyGluGluTyr GTGCGCTTCGACAGCGACAGGGGCGAGTACCGAGCGGTG
ValArgPheAspSerAspArgGlyGluTyrArgAlaVal GCCGAGCTGGGGCGGCCGGACGCCAAGTACTGGAACAGC
AlaGluLeuGlyArgProAspAlaLysTyrTrpAsnSer CAGAAGGAGATCCTGGAGCGGAGGCGGACCGAGGTGGAC
GlnLysGluIleLeuGluArgArgArgThrGluValAsp ACGTACTGCAGACACAACTACGGGGTCATTGA<u>GAGTTTC</u>
ThrTyrCysArgHisAsnTyrGlyValIle <u>ACtgtgcagcggtcgactt</u>

Fig. 2

Leukemia

|    | EY | TKKECHFFNG | TERVRFLDRY | FHNGEEPVRF | DSDWGEYRAV | TELGRPDAKY | WNSQKDFLEE → | KRAAVDTYCR → | HNYGVG 86 |
|----|----|------------|------------|------------|------------|------------|--------------|--------------|-----------|
| L1 | (  | -----R-S-- | ---------- | -Y-------- | ---------- | A--------- | -----EI--R   | R--TE-----   | ------I   |
| L2 |    | STS------- | ---------- | -Y----TL-  | ---------- | A--------- | -----EI--R   | ----------   | ------I   |
| L3 |    | STS------- | ---------- | -Y-------- | ---------- | A--------- | -----EI--R   | R--TE-----   | ------I   |
| L4 |    | STS------- | ---------- | -Y-------- | ---------- | A--------- | -----EI--R   | R--TE-----   | ------I   |
| L5 |    | S-S------- | ---------- | YT----N--- | -------F-- | A------EQ  | ----------S  | R--T------   | ------F   |
| L6 |    | S-S------- | ---------- | YT----N--- | -------F-- | A------EQ  | ----------S  | R--T------   | ------I   |
| L7 |    | H-S-R-S--- | -------Y-- | -Y-------- | ----N--F-- | A---RS-E-  | ----------Q  | T--E------   | ------F   |
| L8 |    | A-S------- | ---L-E---- | -Y-------- | -------F-- | A---RS-E-  | ----------Q  | T--E------   | ------I   |
| L9 |    | -------S-- | -------Y-- | -Y-------- | -------F-- | A-----E-   | ----------S  | R--T------   | ------I   |
| L10|    | R-S-R-S--- | -------Y-- | -Y-------- | ----G--F-- | A---RS-E-  | -----EL--R   | R--T------   | ------F   |
| L11|    | R-S-R-S--- | ---------- | YT----N--- | ----N--F-- | A------EQ  | -----EL--R   | R--TE-----   | ------F   |
| L12|    | S-S------- | ---------- | YT----N--- | -------F-- | A---RS-E-  | -----EL--R   | R--TE-----   | ------I   |
| L13|    | -------S-- | ---L-E---- | -Y-------- | -------F-- | A---RS-E-  | -----EL--R   | R--TE-----   | ------I   |
| L14|    | H-S-R-S--- | ---L-E---- | -Y-------- | -------F-- | A---RS-E-  | -----EL--R   | T--E------   | ------F   |
| L15|    | STS------- | ---------- | -Y-------- | -------F-- | A---RS-E-  | ----------S  | T--E------   | ------F   |
| L16|    | H-S------- | ---------- | YT----N--- | -------F-- | A------EQ  | ----------Q  | T--E------   | ------F   |
| L17|    | -------S-- | ---------- | YT----N--- | -------F-- | A------EQ  | ----------Q  | R--TE-----   | ----R-    |
| L18|    | R-S-R-S--- | -------Y-- | -Y-------- | -------F-- | A---RS-E-  | ----------S  | ---E-N-V--   | ------F   |
| L19|    | YRS------- | ---L-E---- | ------A--- | -------F-- | -----A-EQ  | ----NI--Q    | R--T------   | ------F   |
| L20|    | A-S------- | ---------- | YT----N--- | -------F-- | --------   | ----------S  | R--T------   | ------F   |
| L21|    | S-S------- | ---------- | YT----N--- | -------F-- | -------EQ  | ----------S  | R--T------   | ------F   |
| L22|    | S-S------- | ---L-E---- | -Y-------- | -------F-- | -------EQ  | ----------S  | R--T------   | ----------|
| L23|    | STS------- | ---------- | -Y----TL-  | -------F-- | A---------  | -----EI--R   | ----------   | ----------|

Fig. 3

| | EY | TKKECHFFNG | TERVRFLDRY | FHNGEEFVRF | DSDWGEYRAV | TELGRPDAKY | WNSQKDFLEE | KRAAVDTYCR | HNYGVG |
|---|---|---|---|---|---|---|---|---|---|
| | 8 | | | | | | → | → | 86 |
| Healthy not developing leukemia | --- | ---------- | ---------- | ----YA--- | ---------- | A----RS-E- | ----EI--Q | T--E------ | -----I |
| H1 | --- | STS------- | ---------- | -Y----TL- | ---------- | A--------- | ----EI--R | ---------- | ------ |
| H2 | --- | H-S------- | ---------- | -Y-----Y- | -----F---- | A--------- | ----EL--R | R--TE----- | -----F |
| H3 | --- | STS------- | ---------- | -Y-----Y- | -----F---- | A----RS-E- | ----EI--R | R--TE----- | -----I |
| H4 | --- | H-S------- | ---------- | -Y-----Y- | -----F---- | A--------- | ----EI--R | R--TE----- | -----I |
| H5 | --- | S-S------- | ---------- | YT----N-- | -----F---- | A-----E--- | ----EI--R | R--T------ | -----F |
| H6 | --- | H-S------- | ---------- | -Y-----Y- | -----F---- | A-----EQ-- | ----EI--S | ---------- | -----I |
| H7 | --- | H-S------- | -----Y---- | -Y----TL- | ---------- | A-----E--- | ----EL--R | R--TE----- | -----F |
| H8 | --- | STS------- | ---------- | -Y----TL- | ---N------ | A----RS-E- | ----EI--R | ---N------ | ------ |
| H9 | --- | ---R------ | ---------- | -Y----TL- | ---------- | A----RS-E- | ----EL--R | R--TE----- | -----F |
| H10 | --- | H-S------- | ---------- | -Y-----Y- | ---------- | A--------- | ----EL--R | ---------- | ------ |
| H11 | --- | H-S------- | ---------- | -Y----TL- | ---------- | A--------- | ----EI--R | ---------- | -----I |
| H12 | --- | R-S--R-S--- | ---------- | -Y----TL- | ---------- | A--------- | ----EI--R | ---N------ | ------ |
| H13 | --- | STS------- | ---------- | -Y----TL- | ---------- | A--------- | ----EI--R | ---N------ | ------ |
| H14 | --- | STS------- | ----E----- | -Y----Y-- | ---------- | A-----E--- | ----EI--R | ---------- | ------ |
| H15 | --- | A-S------- | -----Y---- | -Y----TL- | ---------- | A--------- | ----EL--R | ---------- | -----I |
| H16 | --- | R-S--R-S--- | ---------- | -Y----TL- | ---------- | A--------- | ----EI--R | ---------- | ------ |
| H17 | --- | STS------- | ---------- | -Y----TL- | ---------- | A--------- | ----EI--R | ---------- | ------ |
| H18 | --- | STS------- | ---------- | -Y-----Y- | ---------- | A--------- | ----EI--R | ---------- | ------ |
| H19 | --- | STS------- | ---------- | YT----N-- | -----F---- | A-----EQ-- | ----EI--S | ---------- | -----F |
| H20 | --- | H-S------- | ---------- | -Y-----Y- | -----F---- | A-----E--- | ----EI--R | ---------- | -----I |

METHOD FOR JUDGING THE POSSIBILITY OF THE ONSET OF SHEEP LEUKEMIA

TECHNICAL FIELD

The present invention relates to a method for judging a possibility of the onset of ovine leukemia caused by bovine leukemia virus.

BACKGROUND ART

The major histocompatibility antigens (MHC antigens) are molecules involved in self-nonself differentiation in the defense mechanism of the living body against infection. They are classified into Class I molecule composed of α chain and β2M, and class II molecule composed of α chain and β chain. A groove for trapping an antigen peptide is present on the α1 and α2 domains, and also on the α1 and β1 domains. They are featured to have the T cell receptor recognize only a fragmented peptide trapped in the groove, and thereby achieve cell death (cellular immunity) by CD8+ cells which have recognized the class I antigens, as well as induce mainly antibody production (humoral immunity) by CD4+ cells which have recognized the class II antigens.

The MHC genes constitute a gene group most full of polymorphism, and the locations of pockets, shapes, sizes and properties of the peptide trapping grooves are different among haplotypes. It is considered that association conditions of the trapped fragment peptides may vary depending on these differences, which decide immune response and disease sensitivity of each individual. The correlation between the MHC haplotypes and a resistance to a disease (disease insusceptibility) or a possibility of the onset of a disease (disease susceptibility) has been reported, for example, as to human immune deficiency virus (HIV), human T cell leukemia virus (HTLV) and malaria.

As for the bovine MHC (BoLA) class II genes, existence of DQA, DQB, DRA, DRB, DNA, DOB, DYA, and DYB genes has been estimated. DRB3, inter alia, which is one of the three genes (DRB1 to B3) identified on the DRB genetic locus, has been known to encode a functional protein, and existence of 73 alleles has been revealed so far. However, there is almost no report about correlation between bovine infectious diseases and the bovine MHC (BoLA) haplotypes.

In particular, as to the bovine leukemia virus (BLV), which has the gene pX that regulates virus proliferation in the same manner as the human immunodeficiency virus (HIV) and is a retrovirus most related to HTLV-I, a research group in the United States has reported its relationship with the bovine MHC (BoLA) haplotypes mainly focusing disease resistance; however, its relationship with possibility of onset of the leukemia has not been reported. The ratio of cattle infected by this virus (infection rate in Japan) is 10–20%, and 1–2% of the infected cattle develops extremely malignant endemic bovine leukemia to die after a long latent period of 10–15 years. Therefore, economic loss of stockbreeders caused by the virus is very serious. If a possibility of the onset of a cattle after BLV infection can be evaluated by the analysis of bovine MHC (BoLA) haplotypes, it becomes possible to preliminarily select disease resistant cattle for bleeding, and it is expected that extremely safe cattle breeding can be continued.

The inventors of the present invention analyzed the structure of DRB gene locus among the bovine MHC (BoLA) class II genes, and revealed the structures of DRB3 gene (BoLA-DRB3) and its gene product (Biochem. Biophys. Res. Commun., 209, pp.981–988, 1995). The inventors further studied the function of the gene and found that a certain portion, whose amino acid sequence is distinctly different between a cattle developing the leukemia and a cattle not developing the disease, is present in the gene product from the second exon (β1 domain) of BoLA-DRB3 showing particularly noticeable polymorphism. They also found that the amino acid substitutions directly correlated with disease susceptibility to BLV. Furthermore, they found that a cattle, which has homozygous alleles comprising an amino acid sequence: Val-Asp-Thr-Thy at the position defined by the amino acid numbers of from 75 to 78 of the β1 domain of the bovine MHC Class II DRβ chain, can be judged to have a possibility of the onset of the leukemia (the specification of Japanese patent application No. 8-190933 filed on Jul. 19, 1996; the 19th Congress of the Molecular Biology Society of Japan, Sapporo-shi, Aug. 28, 1996, Presentation No. 3-P-1124, Abstracts p.526 published on Jul. 25, 1996).

It has been known that a sheep is also infected by the bovine leukemia virus to cause ovine leukemia. The virus causes three pathologic states in bovines as natural hosts, i.e., antibody-positive healthy condition not developing the disease, persistent lymphocytosis (PL), and endemic bovine leukemia, which is B lymphoma, after a long latent period. When sheep are infected, they are featured to show only two pathological stages, i.e., healthy condition not developing the disease and symptomatic leukemia, and the onset is observed in a shorter period. Therefore, sheep can be used as animals for experimental infection by the bovine leukemia virus, and useful for experiments to evaluate effectiveness of vaccines (Aida, Y. et al., Am. J. Vet. Res., 50, pp.1946–1951, 1989; Aida, Y. et al., Jikken Igaku [Experimental Medicine], Extra Volume, "AIDS and ATL, from Molecular Level Consideration to Prevention and Treatment", 11(5), pp.547–557, 1993). In addition, canceration (malignant transformation) cannot be induced in cultured cells in vitro by bovine leukemia virus infection, whereas malignant transformation can be readily induced in sheep by the virus inoculation, and therefore, sheep are indispensable for estimation of ability of malignant transformation of the bovine leukemia virus.

However, when sheep are used for evaluation of effectiveness of vaccines against the bovine leukemia virus, a problem arises in that experimental data vary and evaluation of experimental results become difficult, which is a cause of lowering efficiency of vaccine developments. The variety may possibly be caused by MHC (OLA) haplotypes; however, correlation between the ovine haplotypes and onset of the leukemia has not been reported so far. If resistance to the onset of the leukemia caused by the bovine leukemia virus can be surely predicted in an ovine individual, and if ovine individuals having constant immune response can be selected, it may be possible to markedly increase efficiency of the development of vaccines against the bovine leukemia virus.

DISCLOSURE OF THE INVENTION

Accordingly, an object of the present invention is to elucidate the relationship between infection or disease development of the bovine leukemia virus (BLV) in sheep and the ovine MHC (OLA) haplotypes, and to provide a method for convenient judgement of a possibility of the onset of leukemia of an ovine individual caused by the bovine leukemia virus (BLV) by means of genetic engineering techniques. Another object of the present invention is to provide a primer set useful for the aforementioned method for judgement.

The inventors of the present invention conducted various studies to achieve the foregoing objects. As a result, they found that a specific amino acid sequence in the β1 domain of the ovine MHC (OLA) Class II DRβ chain correlated with the onset of the ovine leukemia, and achieved the present invention.

The present invention thus provides a method for judging a possibility of the onset of ovine leukemia caused by bovine leukemia virus (BLV), wherein an ovine individual, in which an amino acid sequence defined by the amino acid numbers of 70 and 71 of the β1 domain of the ovine MHC Class II DRβ chain is Ser-Arg or Gln-Thr, is judged to have a risk of the onset of the leukemia, or a method for judging a possibility of the onset of ovine leukemia caused by bovine leukemia virus, wherein an ovine individual, in which an amino acid sequence defined by the amino acid numbers of 70 and 71 of the β1 domain of the ovine MHC Class II DRβ chain is Arg-Lys, is judged to have resistance to the onset of the leukemia. According to preferred embodiment of the present invention, the aforementioned methods are applied to sheep that are experimentally infected by the bovine leukemia virus.

According to preferred embodiments of the methods of the present invention, there are provided the aforementioned method wherein an ovine individual, in which an amino acid sequence defined by the amino acid numbers 70 and 71 of the β1 domain of the ovine MHC Class II DRβ chain is Ser-Arg or Gln-Thr for both of the alleles, is judged to have a risk of the onset of the leukemia; and the aforementioned method wherein an ovine individual, in which an amino acid sequence defined by the amino acid numbers 70 and 71 of the β1 domain of the ovine MHC Class II DRβ chain is Arg-Lys for both of the alleles, is judged to have resistance to the onset of the leukemia.

According to another embodiment of the methods of the present invention, there is provided a method for judging a possibility of the onset of ovine leukemia caused by the bovine leukemia virus, which comprises the steps of:
(1) amplifying genomic DNA isolated from an ovine individual by the polymerase chain reaction (PCR) to prepare a PCR product containing a DNA coding for a part or full length of the β1 domain of the ovine MHC Class II DRβ chain, and
(2) judging that the ovine individual, in which an amino acid sequence corresponding to the amino acid numbers of 70 and 71 of the β1 domain of the ovine MHC Class II DRβ chain is Ser-Arg or Gln-Thr in the amino acid sequence encoded by the DNA contained in the PCR product, has a risk of the onset of the leukemia, or judging that the ovine individual, in which an amino acid sequence corresponding to the amino acid numbers of 70 and 71 of the β1 domain of the ovine MHC Class II DRβ chain is Arg-Lys in the amino acid sequence encoded by the DNA contained in the PCR product, has resistance to the onset of the leukemia.

According to preferred embodiments of the method of the present invention, there are provided the aforementioned method which is applied to ovine individuals infected by the bovine leukemia virus; the aforementioned method wherein an ovine individual, in which an amino acid sequence defined by the amino acid numbers 70 and 71 of the β1 domain of the ovine MHC Class II DRβ chain is Ser-Arg or Gln-Thr for both of the alleles, is judged to have a risk of the onset of the leukemia; and the aforementioned method wherein an ovine individual, in which an amino acid sequence defined by the amino acid numbers 70 and 71 of the β1 domain of the ovine MHC Class II DRβ chain is Arg-Lys for both of the alleles, is judged to have resistance to the onset of the leukemia.

According to the present invention, there are further provided the aforementioned methods which utilize a primer set consisting of:

A primer:
5'-TGTAAAACGACGGCCAGTCTCTCTCTGCAGCA-CATTTCCT-3' (SEQ ID NO:1)

B primer:
5'-CAGGAAACAGCTATGACCCGCCGCTGCACAG-TGAAACTC-3'; (SEQ ID NO:2)

and a primer set used for judging a possibility of the onset of ovine leukemia caused by the bovine leukemia virus, which consists of the aforementioned A primer and B primer.

BRIEF DESCRIPTION OF THE DRAWINGS

FIG. 1 shows the results obtained by amplifying a gene corresponding to the second exon of the gene for the β1 domain of the ovine MHC Class II DRβ chain (OLA-DRB1) by using a primer set (2) consisting of:

A primer:
5'-GGAATTCCTCTCTCTGCAGCACATTTCCT-3' (SEQ ID NO:3)

B primer:
5'-AAGTCGACCGCTGCACAGTGAAACTC-3' (SEQ ID NO:4)

as a set of primers introduced with restriction endonuclease cleavage sites, subcloning the PCR product, and then sequencing one of the alleles, as well as a deduced amino acid sequence. In the figure, the underlined sequences correspond to the locations of the PCR primers.

FIG. 2 show the results of comparison of amino acids of the β1 domain of the ovine MHC Class II DRβ chain (amino acid sequences defined by the amino acid numbers from 8 to 86) derived from sheep that were infected by the bovine leukemia virus and developed the leukemia (16 sheep). Amino acids are indicated as one-letter symbols in the figure, and arrows on the top indicate the positions of amino acid Nos. 70 and 71.

FIG. 3 show the results of comparison of amino acids of the β1 domain of the ovine MHC Class II DRβ chain (amino acid Nos. from 8 to 86) derived from sheep that were infected by the bovine leukemia virus but not developed the leukemia (12 healthy sheep that did not develop the disease). Amino acids are indicated as one-letter symbols in the figure, and arrows on the top indicate the positions of amino acid Nos. 70 and 71.

BEST MODE FOR CARRYING OUT THE INVENTION

The method of the present invention relates to a method for judging a possibility of the onset of leukemia of an ovine individual infected by the bovine leukemia virus, or a possibility of the onset of leukemia of an ovine individual not infected by the bovine leukemia virus when the individual is infected by the virus in future. Sheep are not natural hosts of the bovine leukemia virus and scarcely infected by the virus in nature; however, experimental infections can be established. According to a preferred embodiment of the present invention, genomic DNA of an ovine individual is isolated, and a gene coding for a part or the full length of the second exon of the β1 domain of DRβ chain of the ovine MHC Class II (OLA-DRB1) is specifically amplified by the PCR method, and then the resulting PCR product is subjected to a sequencing to deduce the amino acid sequence defined by the amino acid numbers of 70 and 71 of the β1 domain. When an ovine individual, in which the amino acid sequence of the amino acid numbers 70 and 71 is Ser-Arg (SR) or Gln-Thr (QT), is already infected by the bovine leukemia virus, or when the individual will suffer from infection by the bovine leukemia virus, the ovine individual has a possibility of the onset of the leukemia. On the other hand, an ovine individual, in which the amino acid sequence of the amino acid numbers 70 and 71 is Arg-Lys (RK), has resistance to the onset of the leukemia, even when the individual is already infected by the bovine leukemia virus, or when the individual will suffer from infection by the bovine leukemia virus.

In the above judgement, it is also useful to compare the aforementioned amino acid sequences in the alleles (haplotypes) in order to obtain more accurate judgement. When the amino acid sequence of the amino acid numbers 70 and 71 is Ser-Arg or Gln-Thr in both of the alleles (i.e., SR or QT homozygote), or Ser-Arg in one of the alleles and Gln-Thr in the other allele (i.e., SR/QT heterozygote), the ovine individual has a high risk of the onset of the leukemia. On the other hand, when the amino acid sequence of the amino acid numbers 70 and 71 is Arg-Lys in both of the alleles (i.e., RK homozygote), the individual has high resistance to the onset of the leukemia.

The amino acid sequence of the β1 domain of the ovine MHC Class II DRβ chain was reported by Schwaiger et al. (Schwaiger et al., Mol. Biol. Evol., 11, pp. 239–249, 1994), and the sequence information described therein can readily be utilized by those skilled in the art. As for its nucleotide sequence, the sequence information reported by Ballingall et al. (Ballingall, K. T., et al., Animal Genetics, 23, pp.347–359, 1992) can be utilized. For reference, results obtained by amplifying genomic DNA isolated from an ovine individual by using:

A primer:
      5'-GGAATTCCTCTCTCTGCAGCACATTTCCT-3' (SEQ ID NO:3) and

B primer:
      5'-AAGTCGACCGCTGCACAGTGAAACTC-3' (SEQ ID NO:4)

to obtain a PCR product corresponding to the second exon of the gene for the β1 domain of the ovine MHC Class II DRβ chain (OLA-DRB1), subcloning the PCR product, and then sequencing one of the alleles are shown in FIG. 1, together with a deduced amino acid sequence.

Sheep to be judged by the methods according to the present invention are not particularly limited. The methods may be applied to any sorts of sheep so long as they may be infected by the bovine leukemia virus and have a possibility of developing the leukemia owing to the infection. More specifically, examples include wild sheep such as Mouflon and Red Mouflon, Chinese sheep such as Hu and Mongolian, West Asian sheep such as Blackhead Persian and Karakul, English sheep such as Soay, Manx Loghtan, Jacob, and Suffolk, European (Continental) sheep such as Texel and Churro, Oceanian sheep such as Australian Merino and Corriedale, and the like. However, breeds are not limited to these examples. Whether or not an ovine individual is infected by the bovine leukemia virus can be readily verified by a test for detecting anti-bovine leukemia virus antibody in serum, or a test using an anti-virus antibody.

As a sample for preparing genomic DNA from ovine individuals, peripheral blood, organ and the like can be utilized. For example, a tissue section of the lymph node and other may be used as the organ. As methods for preparing genomic DNA from the sample mentioned above, any methods available to those skilled in the art can be employed. When peripheral blood leucocytes or peripheral blood lymphocytes are used as a sample, for example, the method of Hughes et al. (Hughes, S. H., Cell, 15, pp.1397–1410, 1978) may be applied. When an organ is used, for example, a frozen tissue section may be sliced by using scissors, and then treated by the sodium dodecylsulfate and phenol-chloroform method (Mcknight, G. S., Cell, 14, pp.403–413, 1978). The simplified extraction of genomic DNA from cells may also be used, whose details are described in the examples.

As primers used for amplifying the resulting genomic DNA by the PCR method, any primers may be used so long as they can amplify a DNA coding for a partial amino acid sequence of the β1 domain of the DRβ chain of the ovine MHC Class II comprising amino acid numbers of 70 and 71 or a DNA containing a gene coding for the full length of the β1 domain. An example of a primer set most suitably used for the methods of the present invention includes primer set (1):

A primer:
      5'-TGTAAAACGACGGCCAGTCTCTCTCTGCAG-CACATTTCCT-3' (SEQ ID NO:1); and B primer:
      5'-CAGGAAACAGCTATGACCCGCCGCTGCACA-GTGAAACTC-3'(SEQ ID NO:0)

which enables direct sequencing methods such as the cycle sequencing and the Dynabeads DNA direct sequencing. Another example of a primer set introduced with a restriction endonuclease cleavage site includes primer set (2):

A primer:
      5'-GGAATTCCTCTCTCTGCAGCACATTTCCT-3'; (SEQ ID NO:3) and

B primer:
      5'-AAGTCGACCGCTGCACAGTGAAACTC-3' (SEQ ID NO:4).

However, primers which may be used for the amplification are not limited to the forgoing examples.

An amount of DNA used for the PCR method can be appropriately chosen. For example, the amount may be about 0.1–0.5 µg when peripheral blood leucocytes or peripheral lymphocytes are used. As sequencing methods applied to the DNA amplified as described above (the PCR product), any methods available to those skilled in the art may be utilized. For example, the direct sequencing may preferably be used, whose specific examples are described in the examples. Since most of sheep are heterozygotes, the direct sequencing may sometimes fail to determine which of the alleles corresponds to the target sequence. In that case, the PCR product amplified by using the above primer set (2) may be subcloned to carry out the sequencing of only one of the alleles, and the results may be referred to for comparison to enable a definite sequencing of the other allele. To obtain more precise genetic information, it is preferred that both of the alleles from the PCR product are subcloned and each of the nucleotide sequences is determined. The specific method and applicable primers are detailed in the following examples.

EXAMPLES

The present invention will be explained more specifically by referring to examples. However, the scope of the present invention is not limited to the examples set out below.

Example 1

Peripheral blood was collected as a test sample from an ovine individual by using a syringe containing an anticoagulant, and the blood was centrifuged under conditions of 4° C. and 3,000 rpm for 20 minutes to obtain a leucocyte layer. The separated leucocyte layer was washed with phosphate buffered saline (PBS) and centrifuged to obtain a pellet, which was used as a sample of peripheral blood leucocyte. Peripheral blood lymphocytes were also obtained by the method of Miyasaka et al. (Miyasaka, M. and Trnka, Z., Immunological Methods, Vol.3, pp.403–423, 1985, Academic Press, N.Y.) from peripheral blood obtained in the same manner as described above, and a sample of peripheral lymphocyte was prepared by obtaining a pellet as described above. A BLV infected cell suspension was centrifuged under conditions of 4° C. and 1,100 rpm for 5 minutes to remove a culture medium, and the cells were washed with PBS and centrifuged to obtain a pellet as a sample. In addition, tissue sections were isolated from the lymph node and a tumor tissue of a sheep that developed BLV infection lymphosarcoma, and rapidly frozen in liquid nitrogen without immobilization, and then stored at −80° C. as samples of tissue sections.

Each of the above sample cells were washed twice with PBS in a 1.5 ml-microcentrifuge tube, and the precipitated cells were suspended again in PBS by using a vortex mixer. To 1×10$^6$ cells, 200 μl of 1×PCR buffer [10 mM Tris-HCl (pH 8.3), 50 mM KCl, 2.5 mM MgCl$_2$, 0.5% Tween-20] and 1 μl of Proteinase K (20 mg/ml) were added, and the cells were suspended again by using a vortex mixer and incubated at 56° C. for 45–60 minutes. The mixture was further treated at 95° C. for ten minutes, and cooled on ice for 5 minutes or more. About 5–10 μl of the reaction mixture was used for amplification by PCR.

The genome DNA was dissolved in 50 μl of 1×PCR buffer [10 mM Tris-HCl (pH 8.3), 50 mM KCl, 1.5 mM MgCl$_2$, 0.001% (w/v) gelatin] containing 200 μM of each dNTP, 0.2–0.4 μM of primers, and 2.5 units of Taq polymerase (Gene Amp Kit; Perkin-Elmer Cetus), and then subjected to amplification by 25 cycles, each cycle consisting of treatments at 94° C. for 1 minute, at 61° C. for 1 minute, and at 72° C. for 1 minute, and then further treated at 72° C. for 5 minutes. As the primers, the following primers were used:

A primer: 5'-TGTAAAACGACGGCCAGTCTCTCTCTGCAG-CACATTTCCT-3' (SEQ ID NO:1)

B primer: 5'-CAGGAAACAGCTATGACCCGCCGCTGCACA-GTGAAACTC-3' (SEQ ID NO:2)

which can specifically amplify the β1 domain of the ovine MHC Class II DRβ chain (β1 domain of OLA-DR β: the second exon of DRB1 gene) by the PCR method. Specific biotinylation was introduced into the 5' end of the B primer. These primers can be suitably used for the cycle sequencing.

20 μl of DYNABEADS M-280 Streptoavidin Dynal A.S, N-0212, Oslo, Norway) was washed with 100 μl of 2×binding-washing buffer (B&W buffer: 10 mM Tris-HCl (pH 7.5), 1.0 mM EDTA, 2M NaCl, 0.1% Tween-20), and the beads were suspended again in 80 μl of 2×B&W buffer. The above PCR product (50 μl) was added to the bead suspension and mixed by gentle pipetting, and then incubated at room temperature for 15 minutes with slow rotation using a wheel rotator. The tube containing immobilized PCR product was put on a magnet (Dynal MPC) and the supernatant was removed by using a pipette, and then 100 μl of 2×B&W buffer was added to wash the beads. The supernatant was removed again by using a magnet, and the residue was suspended in 50 μl of 0.1 M NaOH prepared just before use.

The beads with immobilized biotinylated chains were gathered on the tube wall by using a magnet and the supernatant was removed, and then the beads were washed once with 50 μl of 0.1 M NaOH and three times with 100 μl of 1×B&W buffer, and then once with 50 μl of TE buffer. In every operation, the beads were resuspended with smooth strokes. After washing with 100 μl of distilled water, the supernatant was removed, and distilled water was added to the residue to adjust the volume for the use in a sequencing. The sequencing was performed by using BcaBEST Dideoxy Sequencing Kit (Takara Biomedicals) and according to the conditions described in the attached instruction manual. The following primers were used as sequencing primers.

Forward primer: 5'-TGTAAAACGACGGCCAGT-3' (SEQ ID NO:5)

Reverse primer: 5'-CAGGAACAGCTATGACC-3' (SEQ ID NO:6)

The results are shown in FIGS. 2 and 3 (in the figures, amino acids of number 8 to 86 of the β1 domains of the ovine MHC Class II DRβ are shown). Shown in Table 1 are the results obtained from comparison of the amino acid at numbers 70 and 71 of the amino acid sequence of the β1 domain of ovine MHC Class II DRβ chain derived from ovine individuals infected by the bovine leukemia virus but not developing the leukemia (healthy ovine individuals not developing the disease; 12 sheep) and ovine individuals already developing the leukemia (16 sheep). The symbols of genotype such as RK/RK shown in the tables indicate the amino acid sequences written in one-letter symbols (amino acid numbers 70 and 71 of the β1 domain of the ovine MHC Class II DRβ chain) for the both alleles. The numbers in the table were calculated as number of positive individuals/number of tested individuals. From these results, it can be understood that ovine individuals with Ser-Arg or Gln-Thr as the amino acid sequence identified by the amino acid numbers 70 and 71 have a risk of the onset of the leukemia, and individuals having the amino acid sequences in both of the alleles (SR or QT homozygote and SR/QT heterozygote) have a particularly high risk of the onset of the leukemia. On the other hand, it can also be understood that ovine individuals with Arg-Lys as the amino acid sequence identified by the amino acid numbers 70 and 71 have resistance to the onset of the leukemia, and individuals with the amino acid sequence in both of the alleles have particularly high resistance to the onset of the leukemia.

TABLE 1

| | Pathology of ovines with experimental BLV infection | | | |
|---|---|---|---|---|
| | Sheep developing leukemia (n = 16) | | Healthy Sheep not developing leukemia (n = 12) | |
| Genotype | n | % | n | % |
| $R^{70}$-$K^{71}$/X* | 6 | 37.50 | 10 | 83.33 |
| $R^{70}$-$K^{71}$/$R^{70}$-$K^{71}$ | 0 | 0 | 6 | 50.00 |
| $R^{70}$-$K^{71}$/$S^{70}$-$R^{71}$ | 3 | 18.75 | 2 | 16.67 |
| $R^{70}$-$K^{71}$/$Q^{70}$-$T^{71}$ | 1 | 6.25 | 1 | 8.33 |
| $R^{70}$-$K^{71}$/$R^{70}$-$R^{71}$ | 2 | 12.50 | 1 | 8.33 |
| $R^{70}$-$K^{71}$/$Q^{70}$-$K^{71}$ | 0 | 0 | 0 | 0 |
| $Q^{70}$-$K^{71}$/X* | 1 | 6.25 | 0 | 0 |
| $Q^{70}$-$K^{71}$/$R^{70}$-$K^{71}$ | 0 | 0 | 0 | 0 |
| $Q^{70}$-$K^{71}$/$S^{70}$-$R^{71}$ | 0 | 0 | 0 | 0 |
| $Q^{70}$-$K^{71}$/$Q^{70}$-$T^{71}$ | 1 | 6.25 | 0 | 0 |
| $Q^{70}$-$K^{71}$/$R^{70}$-$R^{71}$ | 0 | 0 | 0 | 0 |
| $Q^{70}$-$K^{71}$/$Q^{70}$-$K^{71}$ | 0 | 0 | 0 | 0 |
| $S^{70}$-$R^{71}$/X* | 8 | 50.00 | 2 | 16.67 |
| $S^{70}$-$R^{71}$/$R^{70}$-$K^{71}$ | 3 | 18.75 | 2 | 16.67 |
| $S^{70}$-$R^{71}$/$S^{70}$-$R^{71}$ | 4 | 25.00 | 0 | 0 |
| $S^{70}$-$R^{71}$/$Q^{70}$-$T^{71}$ | 0 | 0 | 0 | 0 |
| $S^{70}$-$R^{71}$/$R^{70}$-$R^{71}$ | 1 | 6.25 | 0 | 0 |

TABLE 1-continued

Pathology of ovines with experimental BLV infection

| Genotype | Sheep developing leukemia (n = 16) | | Healthy Sheep not developing leukemia (n = 12) | |
|---|---|---|---|---|
| | n | % | n | % |
| $S^{70}$-$R^{71}$/$Q^{70}$-$K^{71}$ | 0 | 0 | 0 | 0 |
| $Q^{70}$-$T^{71}$/X* | 4 | 25.00 | 1 | 8.33 |
| $Q^{70}$-$T^{71}$/$R^{70}$-$K^{71}$ | 1 | 6.25 | 1 | 8.33 |
| $Q^{70}$-$T^{71}$/$S^{70}$-$R^{71}$ | 0 | 0 | 0 | 0 |
| $Q^{70}$-$T^{71}$/$Q^{70}$-$T^{71}$ | 2 | 12.50 | 0 | 0 |
| $Q^{70}$-$T^{71}$/$R^{70}$-$R^{71}$ | 0 | 0 | 0 | 0 |
| $Q^{70}$-$T^{71}$/$Q^{70}$-$K^{71}$ | 1 | 6.25 | 0 | 0 |
| $R^{70}$-$R^{71}$/X* | 5 | 31.25 | 3 | 25.00 |
| $R^{70}$-$R^{71}$/$R^{70}$-$K^{71}$ | 2 | 12.50 | 1 | 8.33 |
| $R^{70}$-$R^{71}$/$S^{70}$-$R^{71}$ | 1 | 6.25 | 0 | 0 |
| $R^{70}$-$R^{71}$/$Q^{70}$-$T^{71}$ | 0 | 0 | 0 | 0 |
| $R^{70}$-$R^{71}$/$R^{70}$-$R^{71}$ | 2 | 12.50 | 2 | 16.67 |
| $R^{70}$-$R^{71}$/$Q^{70}$-$K^{71}$ | 0 | 0 | 0 | 0 |

*X represents arbitrary amino acids at positions 70 and 71

INDUSTRIAL APPLICABILITY

A possibility of the onset of the leukemia caused by the bovine leukemia virus and a resistance thereto of an ovine individual can be surely predicted, and ovine individuals having constant immune response can be selected by the methods of the present invention. Therefore, the invention enables estimation of resistance of ovine hosts against various infectious diseases. Furthermore, sheep that cause canceration (malignant transformation) in a short period of time after infection by the bovine leukemia virus can be specifically selected for the use of evaluation of vaccines against the bovine leukemia virus, which enhances accuracy of the evaluation and efficiency of vaccine development. In addition, sheep selected as described above are extremely useful as laboratory animals (leukemia-developing model animals by bovine leukemia virus) for investigation of infection potential, growth ability, in particular, canceration ability (transformation activity) of the bovine leukemia virus.

The bovine leukemia virus is used as a malignant disease model caused by human T-cell leukemia virus (HTLV-I) which is closely related to the bovine leukemia virus. Experimental application of ovine individuals, whose resistance and susceptibility to the onset of the leukemia are evaluated by the method of the present invention, is expected to accelerate researches of adult T-cell leukemia in which relationship between the onset of the leukemia and the human MHC (HLA) polymorphism has not yet been elucidated.

What is claimed is:

1. A method for judging a possibility of the onset of ovine leukemia caused by bovine leukemia virus (BLV), wherein an ovine animal, in which an amino acid sequence defined by amino acid numbers 70 and 71 of the β1 domain of the ovine MHC Class II DRβ chain of an ovine animal is Ser-Arg, respectively, or Gln-Thr, respectively, is judged to have a risk of the onset of ovine leukemia.

2. A method for judging a possibility of the onset of ovine leukemia caused by bovine leukemia virus, wherein an ovine animal, in which an amino acid sequence defined by amino acid numbers 70 and 71 of the β1 domain of the ovine MHC Class II DRβ chain of an ovine animal is Arg-Lys, respectively, is judged to have resistance to the onset of ovine leukemia.

3. The method of claim 1, further comprising determining whether the amino acid sequence is Ser-Arg, respectively, or Gln-Thr, respectively, for both alleles, which indicates a risk of the onset of ovine leukemia.

4. The method of claim 2, further comprising determining whether the amino acid sequence is Arg-Lys, respectively, for both alleles, which indicates resistance to the onset of ovine leukemia.

5. A method for judging a possibility of the onset of ovine leukemia caused by the bovine leukemia virus, comprising:

amplifying genomic DNA isolated from an ovine animal by polymerase chain reaction (PCR) to prepare a PCR product containing DNA coding for a part or full length of the β1 domain of the ovine MHC Class II DRβ chain; and judging that the ovine animal, in which an amino acid sequence corresponding to amino acid numbers 70 and 71 of the β1 domain of the ovine MHC Class II Dβ chain is Ser-Arg, respectively, or Gln-Thr, respectively, in the amino acid sequence encoded by DNA contained in the PCR product, has a risk of the onset of ovine leukemia, or judging that the ovine animal, in which the amino acid sequence corresponding to amino acid numbers 70 and 71 of the β1 domain of the ovine MHC Class II DRβ chain is Arg-Lys, respectively, in the amino acid sequence encoded by DNA contained in the PCR product, has resistance to the onset of ovine leukemia.

6. The method of claim 5, wherein the polymerase chain reaction utilizes a primer set comprising:

primer A: 5'-TGTAAAACGACGGCCAGTCTCTCTCTGCAG-CACATTTCCT-3' (SEQ ID NO: 1);

primer B: 5'-CAGGAAACAGCTATGACCCGCCGCTGCACA-GTGAAACTC-3' (SEQ ID NO: 2).

* * * * *

UNITED STATES PATENT AND TRADEMARK OFFICE
CERTIFICATE OF CORRECTION

PATENT NO.      : 6,316,184 B1
DATED           : November 13, 2001
INVENTOR(S)     : Y. Aida It is certified that error appears in the above-identified patent and that said Letters Patent is hereby corrected as shown below:

<u>Title page,</u>
Item [56], References Cited, FOREIGN PATENT DOCUMENTS, insert -- 8-190933 Japan --

<u>Column 12,</u>
Line 25, "Class II Dβ" should be -- Class II DRβ --.

Signed and Sealed this

Eighteenth Day of March, 2003

JAMES E. ROGAN
*Director of the United States Patent and Trademark Office*

SEQUENCE LISTING

```
<160> NUMBER OF SEQ ID NOS:  6

<210> SEQ ID NO 1
<211> LENGTH: 40
<212> TYPE: DNA
<213> ORGANISM: ovine

<400> SEQUENCE: 1
tgtaaaacga cggccagtct ctctctgcag cacatttcct                             40

<210> SEQ ID NO 2
<211> LENGTH: 39
<212> TYPE: DNA
<213> ORGANISM: ovine

<400> SEQUENCE: 2
caggaaacag ctatgacccg ccgctgcaca gtgaaactc                              39

<210> SEQ ID NO 3
<211> LENGTH: 29
<212> TYPE: DNA
<213> ORGANISM: ovine

<400> SEQUENCE: 3
ggaattcctc tctctgcagc acatttcct                                         29

<210> SEQ ID NO 4
<211> LENGTH: 26
<212> TYPE: DNA
<213> ORGANISM: ovine

<400> SEQUENCE: 4
aagtcgaccg ctgcacagtg aaactc                                            26

<210> SEQ ID NO 5
```

```
-continued

<211> LENGTH: 18
<212> TYPE: DNA
<213> ORGANISM: ovine

<400> SEQUENCE: 5
tgtaaaacga cggccagt                                                  18

<210> SEQ ID NO 6
<211> LENGTH: 18
<212> TYPE: DNA
<213> ORGANISM: ovine

<400> SEQUENCE: 6
caggaaacag ctatgacc                                                  18
```